United States Patent
Müller (10) Patent No.: US 10,994,150 B2
(45) Date of Patent: May 4, 2021

(54) RADIATION APPARATUS FOR THE RADIATION OF HUMAN SKIN

(71) Applicant: WM BEAUTYSYSTEMS AG & Co. KG, Pulheim (DE)

(72) Inventor: Wolfgang Müller, Cologne (DE)

(73) Assignee: WM BEAUTYSYSTEMS AG & Co. KG, Pulheim (DE)

( * ) Notice: Subject to any disclaimer, the term of this patent is extended or adjusted under 35 U.S.C. 154(b) by 53 days.

(21) Appl. No.: 16/108,203

(22) Filed: Aug. 22, 2018

(65) Prior Publication Data

US 2020/0030626 A1     Jan. 30, 2020

(30) Foreign Application Priority Data

Jul. 26, 2018   (EP) .................................... 18185701

(51) Int. Cl.
*A61N 5/06*     (2006.01)

(52) U.S. Cl.
CPC .... *A61N 5/0614* (2013.01); *A61N 2005/0615* (2013.01); *A61N 2005/0639* (2013.01); *A61N 2005/0659* (2013.01); *A61N 2005/0661* (2013.01); *A61N 2005/0663* (2013.01); *A61N 2005/0666* (2013.01); *A61N 2005/0667* (2013.01)

(58) Field of Classification Search
CPC .......... A61N 5/0614; A61N 2005/0661; A61N 2005/0663; A61N 2005/0659; A61N 2005/0615; A61N 2005/0639; A61N 2005/0666; A61N 2005/0667
See application file for complete search history.

(56) References Cited

U.S. PATENT DOCUMENTS

| | | | | |
|---|---|---|---|---|
| 5,534,709 A * | 7/1996 | Yoshimoto | ........... | G01N 23/043 250/588 |
| 6,359,724 B1 * | 3/2002 | Katagiri | .................... | H01S 5/50 359/333 |
| 8,820,981 B2 * | 9/2014 | Jonsson | .................... | F21K 9/23 362/346 |
| 2004/0225339 A1 * | 11/2004 | Yaroslavsky | ........ | A61N 5/0616 607/88 |
| 2006/0152586 A1 * | 7/2006 | Komiya | ............... | A61B 5/0088 348/207.99 |
| 2008/0055584 A1 * | 3/2008 | Pradhan | .................... | G01J 3/10 356/51 |
| 2009/0146086 A1 * | 6/2009 | Manstein | ............... | A61B 18/18 250/504 R |
| 2010/0222852 A1 * | 9/2010 | Vasily | .................. | A61N 5/0603 607/89 |

(Continued)

*Primary Examiner* — Brooke Purinton
(74) *Attorney, Agent, or Firm* — Andrus Intellectual Property Law, LLP (57) ABSTRACT

A radiation device is for the radiation of human skin, preferably the face of a user, in particular at least with radiation in the red light range, with a source of radiation and a filtering device for filtering the radiation emitted by the source of radiation. The filtering device is configured in such a way that the radiation device emits radiation in a wavelength range from 280 to 400 nm and beyond that radiation in a wavelength range of 600 to 700 nm, and that the radiation device emits at least zonally radiation in a wavelength range of a visible color shade of the visible light spectrum and filters further radiation of the visible light spectrum.

20 Claims, 8 Drawing Sheets

(56) References Cited

U.S. PATENT DOCUMENTS

| | | | |
|---|---|---|---|
| 2013/0182234 A1* | 7/2013 | Graupner | G03F 7/70308 355/71 |
| 2014/0288351 A1* | 9/2014 | Jones | A61N 5/0624 600/9 |
| 2015/0060916 A1* | 3/2015 | Nagasaki | H01L 33/504 257/98 |
| 2016/0002384 A1* | 1/2016 | Nacharaju | A61K 9/0014 525/150 |
| 2016/0129279 A1* | 5/2016 | Ferolito | A61N 5/0618 607/89 |
| 2016/0370174 A1* | 12/2016 | Bonino | G01B 11/0683 |
| 2017/0343620 A1* | 11/2017 | Hahn | G01R 33/032 |
| 2019/0336788 A1* | 11/2019 | Mori | A61N 5/0616 |

* cited by examiner

RADIATION APPARATUS FOR THE RADIATION OF HUMAN SKIN

CROSS REFERENCE TO RELATED APPLICATION

This application claims the benefit of and priority from European Patent Application No. EP 18 185 701.2, filed Jul. 26, 2018 in the European Patent Office. The European application is incorporated herein by reference, in entirety.

FIELD

The invention relates to a radiation device for the radiation of human skin, preferably the face of a user, in particular at least with radiation in the red light range, with a source of radiation and a filtering device for filtering the radiation emitted by the source of radiation.

BACKGROUND

It is known that certain cells in the human skin can be stimulated to produce more collagen and elastin as well as enzymes that are mainly responsible for the structure of the skin. This is achieved by using skincare devices with light waves and/or radiation in the range from 550 to 700 nm. In this process, the blood vessels in the skin are stimulated, leading to an oxygenation as well as better detoxification. Hydration increases and the skin's ability to retain moisture improves. Increasing cell activities, improved natural cell repair, as well as cell regeneration lead to a healthier skin appearance.

Facial tanners are known from prior art, which absorb 90-100% of the UV-C radiation in a wavelength range from 100 to 280 nm and which transmit UV radiation in the UV-A range and UV-B range (UV-B range from 280 to 320 nm and UV-A range from 320 to 400 nm). To achieve the aforementioned advantages of radiation in the red light range (in the wavelength range from 600 to 700 nm) in addition to the tanning of the user's face, it is known to arrange LED lamps near and/or on the radiation device which emit in particular radiation with a wavelength of 630 nm. This way, the creation of collagen and elastin can be stimulated in the skin in addition to the desired tanning result.

The additional application of the LEDs to provide radiation in the red light range, however, is associated with a host of disadvantages. The mounting and/or the installation of the LED lights is not only time-consuming but costly as well and/or associated with high installation costs, in particular with regard to the adaptation to the geometry in and/or on the device as well as in the production. Furthermore, the required energy consumption of the entire radiation device including the red light LEDs increases drastically. In addition, users perceive the visible, particularly the very monochrome, radiation component of the LED lights as bothersome. The radiation intensity and/or radiation output of the LEDs cannot be coupled with the intensity of the radiation of the radiation device, so a time-consuming adaptation of the LEDs emitting the radiation in the red light range must be performed. The decrease and/or reduction of the intensity and/or the output of the LEDs and the radiation device that occurs over time is not coupled either, so the lacking adaptation of the LED lights to the radiation device increases over the duration of the use.

SUMMARY

It is the task of this invention to avoid the aforementioned disadvantages in prior art or, at least, to reduce them significantly.

The aforementioned task is solved according to the invention in a radiation device of the aforementioned type in that the filtering device is configured in such a way that the radiation device emits radiation in a wavelength range from 280 to 400 nm and beyond that radiation in a wavelength range from 600 to 700 nm, and that the radiation device emits at least zonally radiation in a wavelength range of a visible color shade of the visible light spectrum and filters further radiation of the visible light spectrum.

The radiation device according to the invention makes it possible to emit UV radiation, in particular UV-A radiation and UV-B radiation, and radiation in the red light range at the same time. The additional installation of LED lights emitting radiation in the red light range can be avoided. According to the invention, the red light can be provided by the radiation device itself. The positive effect on the skin provided by the radiation in the red light range, preferably the stimulated production of collagen and elastin, can, according to the invention, be synergetically combined with the tanning effect generated by the UV radiation. Therefore, the production of collagen and/or elastin in the skin can be stimulated during the tanning of the skin, which leads to an improved and tanned skin appearance of the skin and a natural and clean skin appearance.

Preferably, the entire radiation strength, radiation intensity, and/or radiation output of the radiation device is reduced at least zonally by the at least zonally emission of a visible color shade of the visible light spectrum and the filtering of the further radiation, which improves the tanning result and, in particular, makes it more even. One advantageous side effect here is that users perceive the color shade that is emitted as pleasant and produces a sense of wellbeing.

Furthermore, the at least zonally display of the visible color shade making it easy to demonstrate, in particular detect, the wavelength range emitted by the radiation device. In particular, the area emitting the visible color shade can be arranged on the radiation device in such a way that sensitive areas of the human skin of the user, in particular the face, for example the area around the eyes, are irradiated with a lower radiation strength, radiation output, and/or radiation intensity, preferably in the range of UV radiation. By means of the radiation cone resulting from the emission from the radiation device, an overlapping of the radiation can be achieved in such a way that the tanning result and the skin appearance can be improved in accordance with the objective and purpose.

The visible light spectrum is in a wave range between 380 and 780 nm. Light is the part of the electric radiation that humans can perceive with the naked eye. Light has different color shades, depending in particular on the light's spectral color ranges.

Ultimately, it is clear that radiation can be transmitted by the radiation device in the color shade, radiation in the red light range and/or UV in a wavelength range from 280 to 400 nm across the entire wave range and/or that only some ranges and/or peaks are provided in the aforementioned wavelength ranges.

To emit radiation in the red light range, for example, it suffices when radiation in a wavelength range of 650±20 nm is emitted. Even an emission of the UV radiation in a wavelength range from 320 to 400 nm would be adequate to achieve the desired tanning effect.

The visible color shade is selected in particular from the color ranges that are visible to humans and may, if necessary, be produced by overlapping the spectral color ranges of the light. The visible light spectrum can be subdivided into different spectral color ranges.

Radiation in the red light range between 600 and 700 nm, in particular between 630 to 700 nm, can be provided.

Radiation in the orange light range between 590 and 630 nm can be provided.

Radiation in the yellow light range from 560 to 590 nm can be provided as well.

Furthermore, radiation in the green light range from 490 to 560 nm can be provided.

Radiation in the blue light range can be provided at a wavelength between 450 and 490 nm.

Purple radiation and/or radiation in the purple range can be provided at a wavelength from 400 to 450 nm.

A visible color shade may characterize monochromatic light. Monochromatic light in the narrower sense is a single-color, visible light whose resulting color perception is also referred to as spectral color. The spectral color ranges of the light can merge.

The radiation device emits at least in certain ranges one color of light, whereby one color of light differs from a body color in that the color of light is the color of a self-illuminating source of light, in this case the source of radiation. Color stimulus produced by the color of light is based on a spectral composition of the light. It is composed either of discrete, individual colors of certain wavelengths, from a light mixture of several wavelengths of wavelength ranges, and/or from a continuous spectral range.

Furthermore, the arrangement according to the invention makes it possible for the radiation strength, the radiation intensity, and/or the radiation output of the radiation in the red light range to be coupled with the radiation in the UV wavelength range.

In a particular preferred embodiment, the filtering device is able to filter radiation with a wavelength below 280 nm. It may be provided in particular that a filtering by reducing the radiation intensity by more than 60%, preferably between 70 and 100%, and even more preferably between 90 and 99.99%, occurs for wavelengths below 280 nm. Filtering the aforementioned wavelength ranges of the radiation may lead to a reduction of the radiation strength, the radiation output, and/or the radiation intensity. Particularly preferred is a filtering in which substantially no radiation with a wavelength of below 280 nm is emitted by the radiation device.

The aforementioned filtering of the radiation for a wavelength below 280 nm is particularly advantageous, because radiation with a wavelength below 280 nm does not have an advantageous effect for the improvement of the skin appearance and may even be harmful to the user, in particular the user's skin. Accordingly, any radiation that does not contribute to the tanning of the face is filtered by the filtering device.

Preferably, the filtering device comprises at least one filter disk. The filter disk, in turn, may have a first coating. The first coating is configured in particular so that the aforementioned characteristics of the filtering device regarding the filtering of radiation with a wavelength below 280 nm are guaranteed.

Furthermore, it may be provided in a preferred embodiment that the first coating is arranged on the front side of the filter disk that faces the source of radiation. In particular, the first coating was applied on the front side of the filter disk. The first coating may be provided as a fully formed coat on the filter disk so that the characteristics provided by the first coating are guaranteed across the entire surface of the filter disk.

The filter disk is, in particular, arranged in the radiation device in such a way that the entire radiation of the source of radiation that leaves the radiation device must pass through the filter disk, in particular whereby the radiation is transmitted to the filter disk, absorbed, and/or reflected.

The variable for the permeability of a medium, in this case of the radiation device and/or the filter disk, for electromagnetic waves, in particular light, is the transmission. Transmittance is a material property and is defined on the basis of the quotients between the wave intensity after and before the obstacle. Transmittance is therefore a way to measure the intensity that is let through and may vary from 0 to 1 or respectively from 0% to 100%.

Preferably, the filter disk, in particular the first coating, is designed so that UV radiation, in particular UV-A radiation and UV-B radiation, is transmitted in a wavelength range from 280 to 400 nm and/or radiation in the red light range in a wavelength range between 600 and 700 nm, preferably from 600 to 650 nm, and/or radiation with a wavelength of greater than 700 nm. The transmittance can be greater than or equal to 50% here, preferably between 50 and 10% [sic], and even more preferably between 85 and 98%. The first coating or the filter disk, respectively, is permeable for the aforementioned different wavelength ranges.

A transmission of radiation of greater than 700 nm in the infrared range is particularly advantageous because radiation in the infrared area has positive side effects in the radiation of human skin and, in particular, causes a pleasant, warm sensation on the user's skin. UV radiation in a wavelength range from 280 to 400 nm causes the natural tanning effect in the user's skin.

Furthermore, the filtering device, in particular the filter disk, preferably the first coating, is able to absorb UV radiation in the UV-C range, preferably in a wavelength range from 100 to 280 nm. Here, the degree of absorption may be greater than 0.5, preferably between 0.6 and 1, and even more preferably between 0.8 and 0.99.

The degree of absorption indicates which part of the output of an arriving wave—electromagnetic radiation such as light—is absorbed by a surface, in this case the first coating and/or the filter disk.

The filtering device filters in particular UV radiation in the UV-C range so that the tanning result can be improved.

In a further particularly preferred embodiment of the inventive idea, the filter disk, in particular the first coating, is designed so that UV-B radiation in a wavelength range from 280 to 320 nm is transmitted with a transmittance of less than or equal to 50%, preferably between 0.1 and 50%, and even more preferably between 1 and 8%. The transmitted portion of the UV-B radiation is, in particular, adapted to legal requirements.

Additionally or alternatively, the filter disk, in particular the first coating, may be designed so that UV radiation in a wavelength range from 320 to 400 nm is transmitted with a transmittance of greater than or equal to 40%, preferably between 45 and 95%, and even more preferably between 50 and 70%.

Furthermore, the filter disk, in particular the first coating, may be designed so that radiation in the blue light range and in a wavelength range from 400 to 480 nm is transmitted with a transmittance of greater than or equal to 20%, preferably between 30 and 95%, and even more preferably between 60 and 80%. With the concurrent transmission of radiation in the red light range via the first coating, an overlapping with the radiation in the blue light range may occur so that the user perceives a different color.

In a further particularly preferred embodiment, the filter disk comprises a second coating. The second coating is, in particular, arranged on the first coating, and even more preferably on the surface of the first coating facing away from the front side. Accordingly, the radiation of the source of radiation preferably first comes in contact with the first coating and then with the second coating.

Preferably, the second coating is firmly bonded to the first coating. They may be bonded directly or indirectly. If they are indirectly bonded, at least one further coat and/or layer of the filter disk is provided between the first coating and the second coating.

Furthermore, the second coating may be arranged on the back side of the filter disk facing away from the source of radiation, whereby in particular the second coating is applied on the back side.

Furthermore, the second coating may be designed as a partially formed coating. In particular, the second coating is intermittent. Preferably, the second coating may have the effect that the radiation device is capable of emitting at least zonally radiation in a wavelength range of a visible color shade of the visible light spectrum and filtering further radiation of the visible light spectrum.

Consequently, the filter disk comprises areas provided with both the first coating and the second coating and other areas with only the first coating. Ultimately, it is clear that the filter disk has at least the properties provided by the first coating, in particular when the first coating is applied across the entire surface of the filter disk. In the areas with the second coating, further wavelength ranges can be filtered, overlapped by the properties of the first coating.

The second coating may be designed in such a way that a color shade is shown on the back side of the filter disk—not visible to the user—and/or that a visible color effect of a visible color shade is created.

In addition, the second coating may be applied and/or provided on the filter disk in a grid-shaped, continuous, and/or irregular manner. The areas of the filter disk provided with the second coating are selected so that, in particular with regard to the surface areas of the area covered by the second coating, improved radiation results can be achieved on the human skin irradiated by the radiation device.

Preferably, the second coating can be applied on the back side of the filter disk and/or the first coating by means of a template. The template may be made from glass and/or metal and/or a stone-based and/or heat-resistant material. The free surfaces allow for a partial coating of the filter disk with the second coating.

In terms of the method, it may be provided for the coating of the filter disk with the first and/or the second coating that the coating is performed in a vacuum, preferably a high vacuum. The coating may be performed with dielectric coats and/or coatings. The dielectric coats of the first and/or the second coating allow in particular for the desired transmission, absorption, and/or reflection behavior.

The tests that were performed as the invention was made were able to show that improved tanning results and the production of collagen and elastin that produce natural tanning can be guaranteed by means of an interaction of the first coating and the second coating.

Due to the zonally application of the second coating, individual wavelength ranges and/or monochromatic light can be intentionally made visible to the user so that a control function and/or detection function of the radiation emitted via the radiation device is provided.

Furthermore, a plurality of different second coatings may be provided on the filter disk that differ in terms of their filtering, geometry, coat thickness, and/or their properties, in particular material properties. This way, various visible color shades can be produced on the back side of the filter disk that faces the user.

Preferably, the second coating for the filtering of radiation is designed so that radiation is transmitted in at least one wavelength range of a visible color shade of the visible light spectrum and, preferably, radiation with a wavelength of greater than 700 nm. In particular, further radiation, preferably further radiation of the visible light spectrum, is otherwise reflected and/or absorbed by the second coating. The wavelength range of a visible color shade may, in particular, be radiation in the green light, red light, and/or yellow light range. Ultimately, at least such a wavelength range is transmitted via the second coating that causes a color effect that is perceivable by a user.

Alternatively or additionally, it may be provided that the second coating is designed so that UV radiation in a wavelength range from 100 to 400 nm and/or blue light in a wavelength range from 400 to 480 with a transmittance of less than or equal to 20%, preferably between 0.01 and 50%, and even more preferably between 0.1 and 5%, is transmitted. In particular UV radiation and/or blue light is filtered by the second coating so that radiation transmitted through the second coating preferably has a very low amount of blue light and/or UV radiation.

Furthermore, the second coating is preferably designed so that radiation in the red light range in a wavelength range from 600 to 700 nm and/or radiation with a wavelength range of greater than 700 nm is transmitted with a transmittance of greater than or equal to 50%, preferably between 50 and 100%, and even more preferably between 75 and 85%. Preferably, the second coating transmits radiation in the red light range and radiation with a wavelength of greater than 700 nm in the infrared range. For the user, facing the back side of the filter disk, the areas of the filter disk with the second coating may look particularly red and/or emit red light. This way, it is possible to clearly identify and/or determine that red light is transmitted via the first coating, i.e., in these areas that do not have a second coating, as well. The parts of the radiation that were already filtered by the first coating are further reduced, in particular filtered and/or transmitted, by the second coating.

According to a further embodiment, it may be provided that the second coating transmits UV radiation in a wavelength range from 320 to 400 nm with a transmittance of greater than or equal to 40%, preferably between 45 and 95%, and even more preferably between 50 and 70%. Preferably, the second coating transmits radiation in the red light range, radiation with a wavelength of greater than 700 nm in the range from 320 to 400 nm, and/or radiation in the UV-A and/or UV-B range.

Furthermore, UV radiation is not optically visible to the naked eye of the user facing the back side of the filter disk.

It is of a particular advantage in connection with the present invention when the source of radiation is provided in a reflector device to which a cooling device has been assigned. The reflector device comprises a reflector in which the source of radiation, preferably a radiation lamp, is arranged. The filter device may be assigned to the reflector device, and/or the reflector device comprises the filter device.

The advantage of the present invention is that the reflector device according to the invention may generally correspond in its form and size to a reflector device that is used in prior art with radiation devices for irradiating the user's face. The known reflector device for tanning the face may be easily exchanged for the reflector device according to the invention, and/or the filter device according to the invention may easily be integrated in already existing reflector devices and/or installed on them. This makes it possible to retrofit known facial tanners according to the invention.

Furthermore, it may be alternatively or additionally provided that the filter device comprises a slanted filter mirror that reflects radiation in the wavelength range from 280 to 400 nm, preferably from 280 to 320 nm, and/or radiation in the red light wavelength range from 600 to 700 nm and/or in the wavelength range above 700 nm. Preferably, the reflection factor for the various aforementioned wavelength ranges is greater than or equal to 40%, preferably between 45% and 95%, and even more preferably between 50 and 70%, in particular whereby the filter mirror transmits and/or absorbs otherwise. The filter mirror may be used, in particular, alternatively but also additionally to the filter disk, which may comprise the first coating and/or the second coating. The filter mirror may also be referred to as a reflection disk.

As a filter mirror, a known filter mirror can be used that is impermeable in the red light range and/or that filters radiation in the red light range, which is subsequently treated to produce the filter disk according to the invention. The subsequent treatment provided may be a partial ablation, in particular mechanical and/or chemical, of a layer and/or of layers on the original filter mirror so that the filter mirror is at least zonally and/or partially permeable for radiation in the red light range.

Furthermore, the reflector units and/or the reflector itself may be part of the filter device and, in particular, be designed so that the reflector device reflects, in particular emits, radiation in the wavelength range from 100 to 480 nm, preferably in a wavelength range from 280 to 400 nm, and/or in a wavelength range from 600 to 700 nm and/or in the wavelength range of greater than 700 nm. Preferably, the reflection factor here is greater than or equal to 40%, preferably between 45 and 95%, and even more preferably between 50 and 70%. Furthermore, it can be provided that the reflector device and/or the reflector transmits and/or absorbs otherwise, in particular filters and/or blocks. In this way the desired wavelength range is already filtered by the reflector and/or the reflector device accordingly.

The reflector of the reflector device may, in particular, be coated, preferably with the first and/or second coating. Only those wavelength ranges of the radiation may be emitted that are desired.

Furthermore, the reflector device may comprise a reflection means that is designed so that the radiation emitted by the source of radiation at least essentially hits the reflector entirely.

In a further embodiment, it may be provided that the filtering device, preferably the filter disk, comprises at least one fluorescing layer. The fluorescing layer may have been applied facing away from the front side of the filter disk on the surface of the first coating. The fluorescing layer is, in particular, applied to the back side of the filter disk. The fluorescing layer may furthermore be designed as a partial layer.

Furthermore, the fluorescing layer may be firmly bonded to the coating and, in particular, applied to it. The fluorescing layer may be designed so that, when subjected to radiation, preferably UV radiation in a wavelength range from 280 to 400 nm, it emits and/or sends out radiation in the red light range with a wavelength rage from 600 to 700 nm. The fluorescence of the fluorescing layer can ultimately be stimulated by the UV radiation emitted by the source of radiation.

Preferably, the source of radiation is designed as at least one radiation lamp, in particular as a high-pressure and/or a maximum-pressure gas discharge lamp.

In particular, controllable or uncontrollable, in particular magnetic or electronic, ballasts may be provided. The ballast may preferably dim the source of radiation, in particular the radiation lamp, and/or the source of radiation is capable of being dimmed by the ballast.

Furthermore, it is clear that in the aforementioned intervals and ranges all interim intervals and individual values are comprised and must be considered as essential for the invention, even if these interim intervals and individual values are not specifically provided.

BRIEF DESCRIPTION OF THE DRAWINGS

Further features, advantages, and application possibilities of the present invention are provided in the following description of exemplary embodiments shown in the drawing and the drawing itself. All described and/or illustrated features form, by themselves or in any combination, the object of the present invention, regardless of their summary in the claims and their dependencies.

DETAILED DESCRIPTION OF THE DRAWINGS

Figure 1:
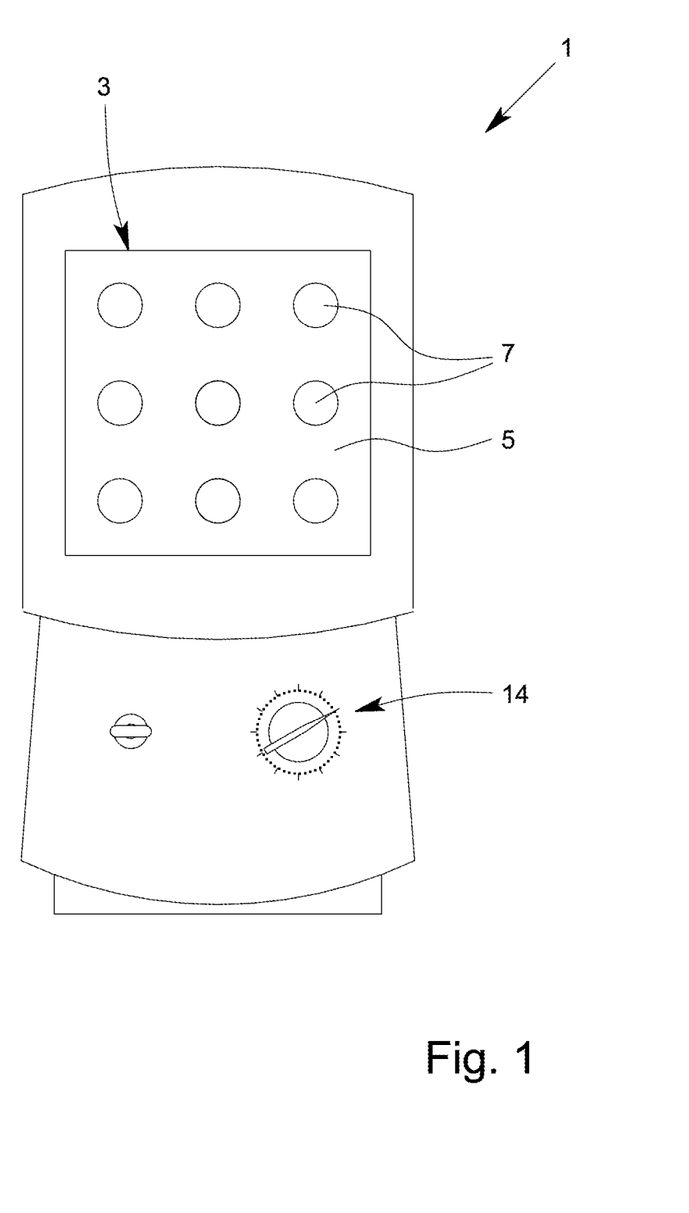
FIG. 1 shows a schematic frontal view of a radiation device according to the invention.
Figure 3:
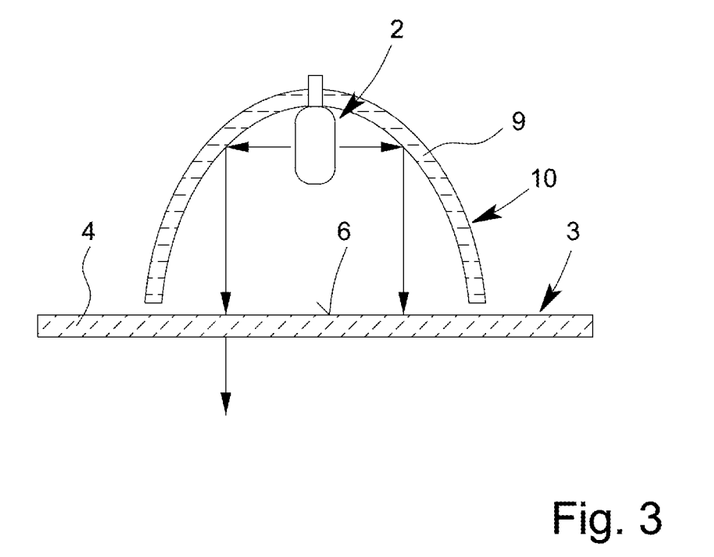
FIG. 3 shows a schematic view of parts of a radiation device according to a first embodiment.

FIG. 1 shows a radiation device 1 for the radiation of human skin with a source of radiation 2, as shown in FIG. 3, and with a filtering device 3 for filtering the radiation emitted by the source of radiation 2.

Figure 2:
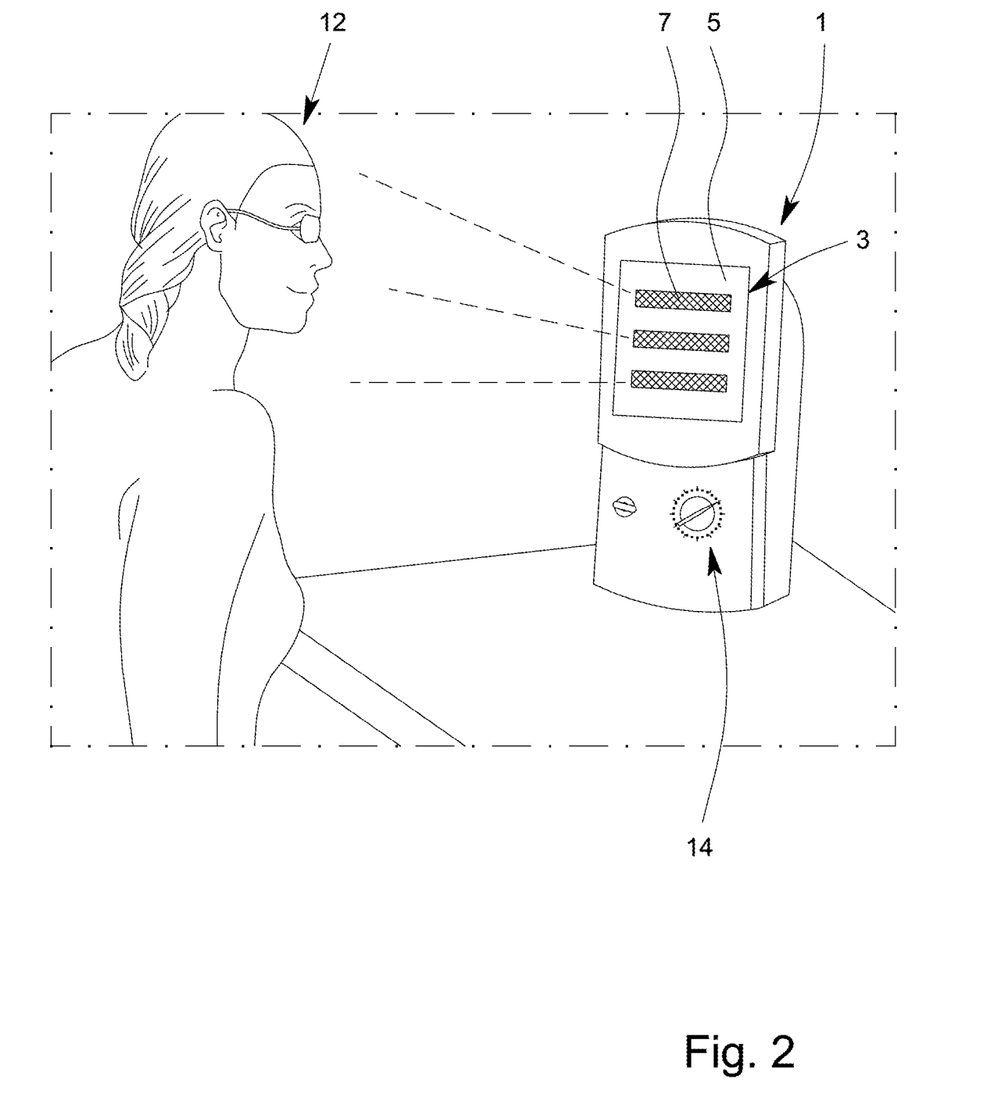
FIG. 2 shows a schematic perspective illustration of a further embodiment of a radiation device according to the invention.

FIG. 2 shows that the radiation device 1 is intended for the radiation of the face of a user 12. The radiation device 1 emits radiation in the red light range, i.e., red light in a wavelength range from 600 to 700 nm. The filtering device 3 shown in the illustrated embodiments is designed in such a way that the radiation device 1 emits radiation in a wavelength range from 280 to 400 nm and beyond that radiation in a wavelength range of 600 to 700 nm, and that the radiation device 1 emits at least zonally radiation in a wavelength range of a visible color shade of the visible light spectrum and filters further radiation of the visible light spectrum. FIGS. 1 and 2 illustrate that the side of the radiation device 1 facing the user 12 provides for areas that transmit radiation in a color shade and filter other radiation from the visible light spectrum.

Figure 10:
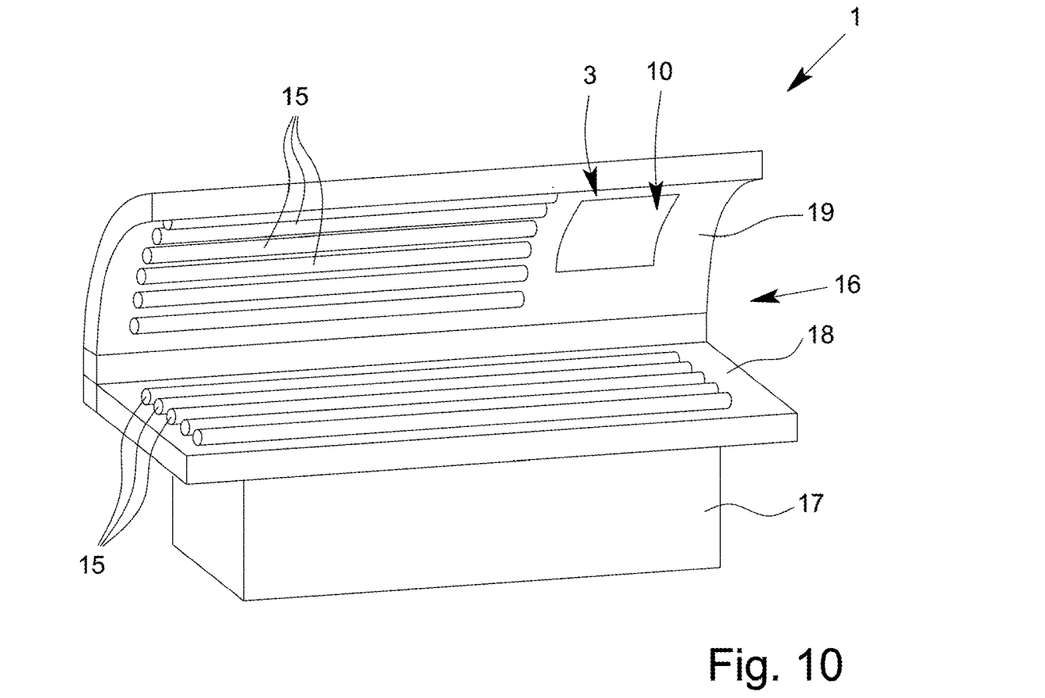
FIG. 10 shows a schematic perspective illustration of a further embodiment of a radiation device according to the invention.

FIG. 10 shows a radiation device 1 for radiation of human skin designed as a sun bed or tanning bed. The radiation device 1 is a so-called tunneling device comprising a substructure 17 and a rotatable top part 19 attached to the substructure 17. The top part 19 can be rotated down to the substructure 17 so that a tunnel is formed in which the user 12 rests during operation. Long low-pressure fluorescent lamps 15 are located below the bed 18 in the substructure 17 and in the top part 19 which are able to emit radiation in the red light range as well.

A filtering device 3 with a filter disk 4, arranged on a reflector device 10, is located in the facial area 16 of the top part 19 of the radiation device 1.

Figure 11:
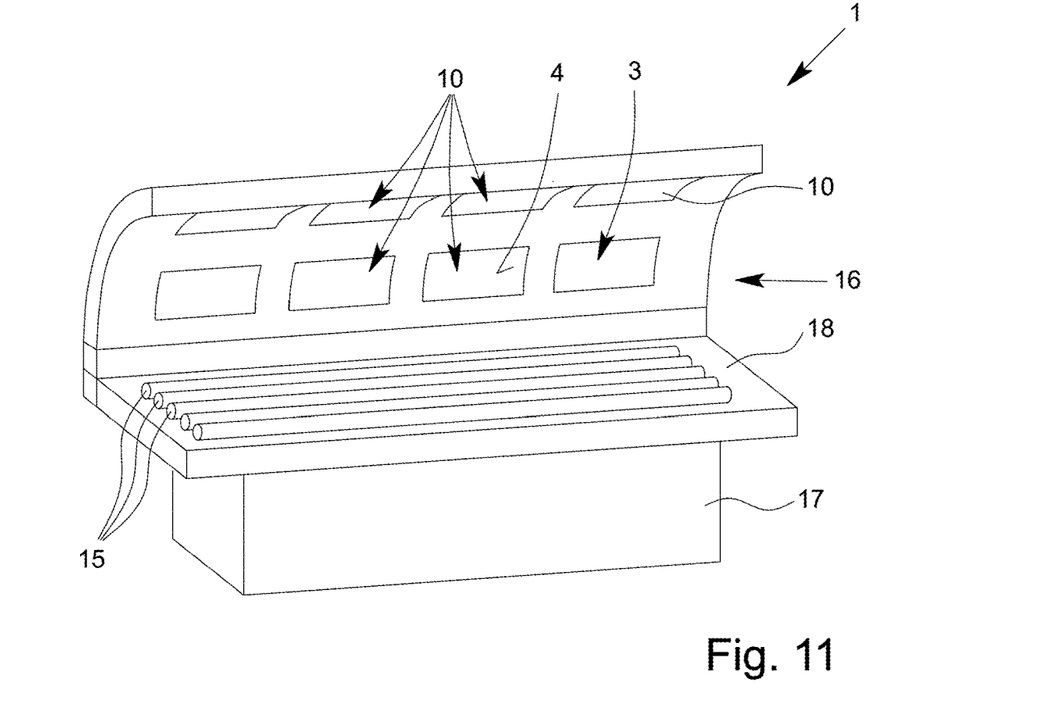
FIG. 11 shows a schematic perspective illustration of a further embodiment of a radiation device according to the invention.

FIG. 11 shows an embodiment in which the area of the top part 19 comprises not just one but a plurality of reflector devices 10 and/or filtering devices 3 of a source of radiation 2, which is not shown here. In the exemplary embodiment that is shown, eight reflector devices 10 and filtering devices 3 are provided, which are arranged in pairs.

What is not shown is that in the substructure 17 as well at least one source of radiation 2 with the corresponding filtering device 3 is provided.

According to the embodiment shown in FIG. 3, the filtering device 3 is designed so that it filters radiation with a wavelength below 100 nm. A filtering requires a reduction of the radiation strength, the radiation output, and/or the radiation intensity especially in the range between 90 and 100%.

Figure 4:
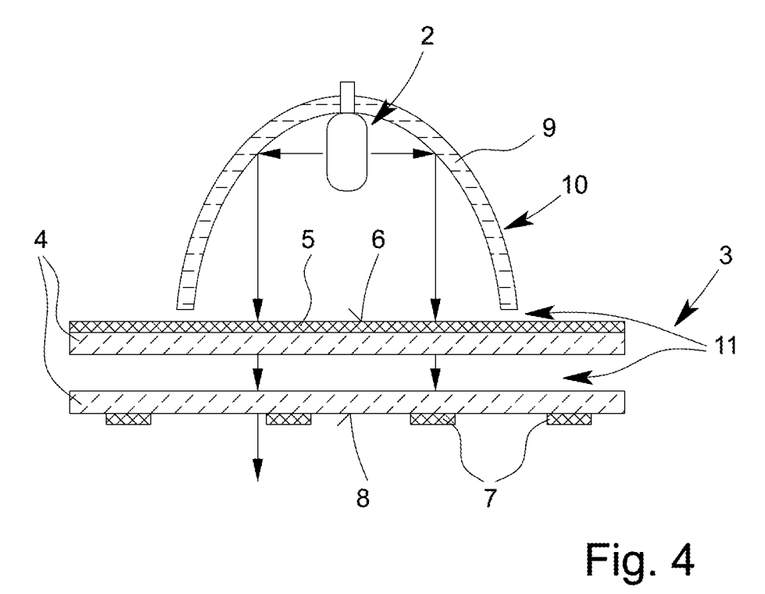
FIG. 4 shows a schematic view of parts of a radiation device according to a second embodiment.

FIG. 4 shows that the filtering device 3 comprises a filter disk 4. According to the exemplary embodiment shown in FIGS. 4 and 5, the filter disk 4, in turn, can be arranged, preferably applied, on the front side 6 of the filter disk 4 facing the source of radiation 2. The first coating 5 may be a fully formed layer, as FIG. 5 makes clear.

Figure 7:
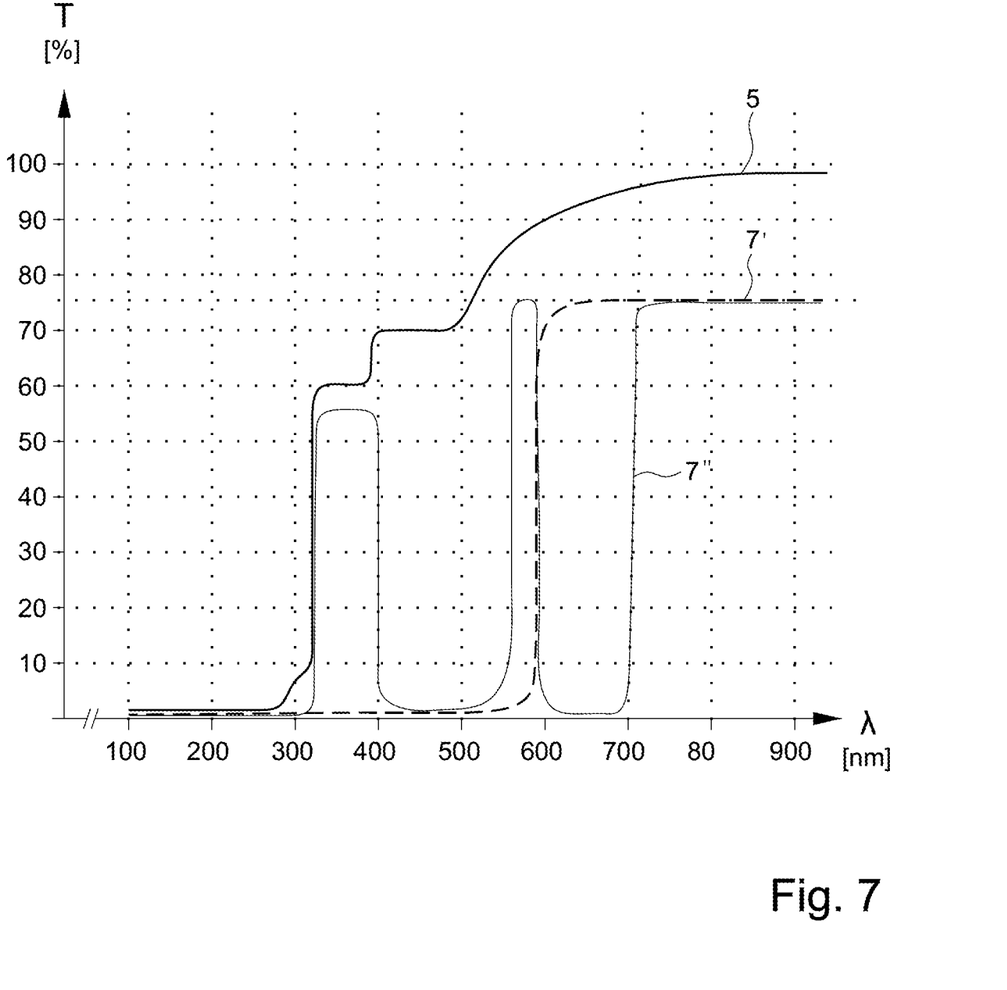

FIG. 7 shows the transmission of the first coating 5 for various wavelength ranges. Lambda and/or the x-axis provides the wavelength in nm, whereby the y-axis shows the transmission and/or the transmittance in percent. According to the behavior shown in FIG. 7, it is provided that the first coating 5 is designed so that the transmission of the UV radiation in a wavelength range from 280 to 400 nm, i.e., UV-A radiation and UV-B radiation, is greater than or equal to 50%. According to the behavior shown in FIG. 7, the transmittance of UV radiation with a wavelength between 280 and 320 nm ultimately ranges between 1 and 8%, on average approximately 5%±3%. UV radiation in a wavelength range from 100 to 280 nm is absorbed, whereby the absorbance ranges from 0.8 to 0.99 according to the behavior shown in FIG. 7.

Furthermore, the first coating 5 is designed so that radiation in the red light range, i.e., radiation with a wavelength of greater than 600 to 700 nm, is transmitted and/or radiated with a transmittance of approximately 95%±5%. Furthermore, radiation with wavelengths of greater than 700 nm is transmitted and preferably not filtered so that the transmittance for radiation with a wavelength of over 700 nm may also amount to 95%±5%.

Furthermore, it may also be provided that the first coating 5 is designed so that UV radiation in a wavelength range from 280 to 400 nm and/or radiation in the red light range in a wavelength range between 600 and 700 nm, preferably from 600 to 650 nm, and/or radiation with a wavelength of greater than 700 nm is transmitted. The transmittance here may be greater than or equal to 50%, and even more preferably between 85% and 95%.

As demonstrated above, FIG. 7 shows that the first coating 5 is designed so that UV-B radiation in a wavelength range from 280 to 320 nm is transmitted with a transmittance of less than or equal to 50%, preferably between 1% and 8%.

Furthermore, the filter disk 4, in particular the first coating 5, may be designed so that UV radiation in a wavelength range from 320 to 400 nm is transmitted with a transmittance of greater than or equal to 40%, preferably between 50 and 70%.

Furthermore, the conduct illustrated in FIG. 7 shows that the filter disk 4, in particular the first coating 5, may be designed so that radiation in the blue light range in a wavelength range from 400 to 480 nm is transmitted with a transmittance of greater than or equal to 20%, preferably between 60% and 80%. Ultimately, it is clear that the behavior of the transmission of the first coating 5 illustrated in FIG. 7 may correspond to the entire radiation behavior of the radiation device 1.

FIG. 4 shows that the filter disk 4 comprises a second coating 7. In the embodiment shown in FIG. 4, ultimately two filter disks 4 are provided, whereby the first filter disk 4 facing the source of radiation 2 comprises a first coating 5 at its front side 6. The second filter disk comprises on the back side 8 facing away from the source of radiation 2 a second coating 7 at least in some areas. A cooling device 11 and/or an air space is provided between the filter disks 4.

Figure 6A:
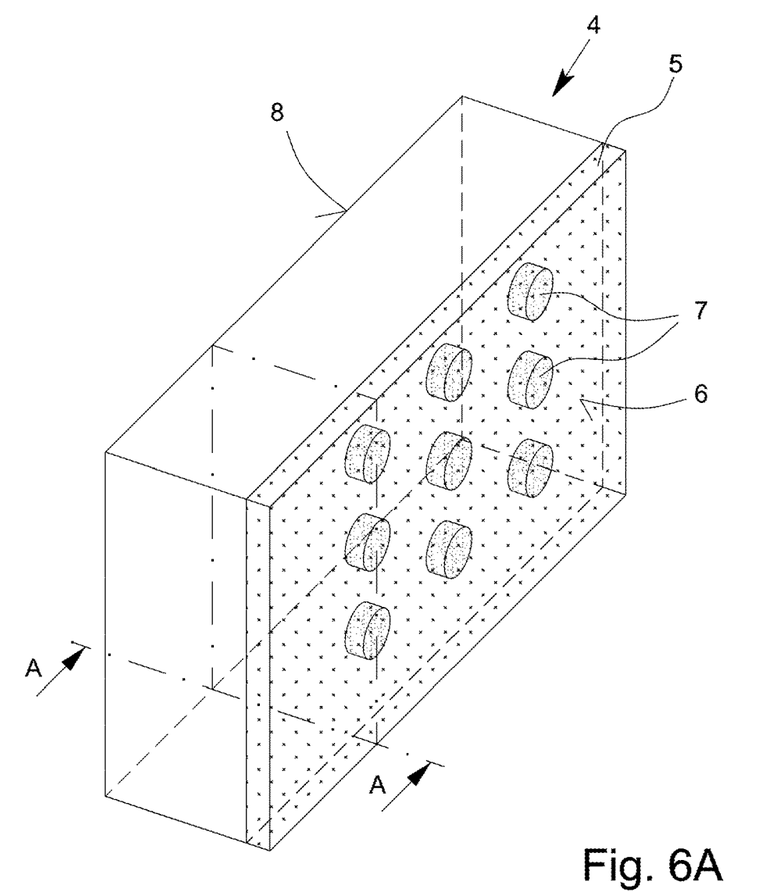
FIG. 6a shows a schematic perspective illustration of a filter disk according to the invention.
Figure 6B:
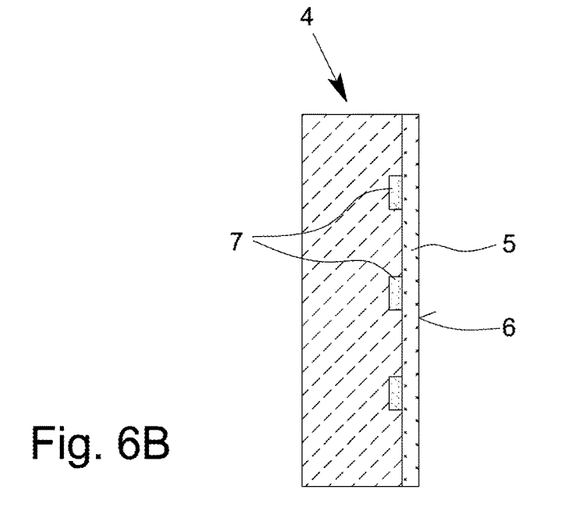
FIG. 6b shows a schematic sectional view along the section A-A from FIG. 6a, FIG. 7 shows an illustration of the transmission of a radiation device according to the invention by means of the wavelength.

In the embodiment shown in FIGS. 6a and 6b, the second coating 7 is arranged on the first coating 5, whereby the second coating 7 is firmly bonded with the first coating 5.

Figure 5:
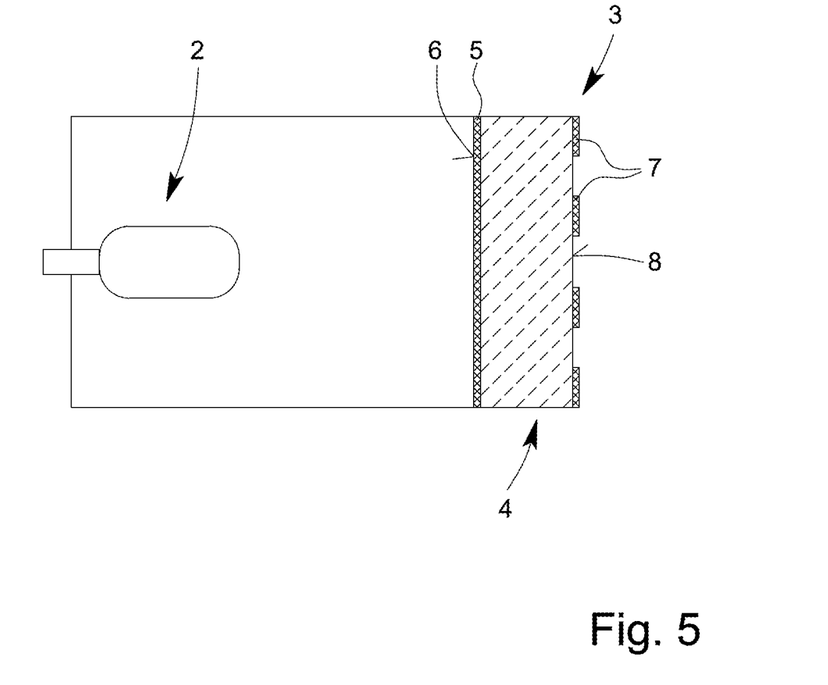
FIG. 5 shows a schematic view of parts of a radiation device according to a third embodiment.

FIG. 5 shows that the second coating 7 is arranged on and in particular applied to the back side 8 of the filter disk 4, facing away from the source of radiation 2, whereby the first coating 5 is provided on the front side 6 of the filter disk 4.

The second coating 7 shown in FIGS. 5 to 6b is designed as a partial layer. The partial second layer 7 is therefore an interrupted layer. Ultimately, a plurality of interrupted and/or partial second coatings 7 may be provided on the filter disk 4 which differ in terms of their material properties and/or functions.

The second coating 7 is designed for the filtering of radiation, whereby radiation in at least one wavelength range of a visible color shade of the visible light spectrum is transmitted. As the visible color shade, radiation in the green light wavelength range, red light wavelength range and/or yellow light wavelength range may be provided. The green light range is provided in particular at a wavelength from 490 to 560 nm, the yellow light range from 560 to 590 nm, and the red light range from 600 to 700 nm, preferably from 630 to 700 nm. Furthermore, the second coating 7 may transmit radiation with a wavelength of greater than 700 nm, in particular whereby otherwise the second coating 7 reflects and/or absorbs.

Through those areas of the filter disk 4 that only comprise the first coating 5, the entire radiation device 1 may therefore transmit the filtered radiation via the first coating 5. In those areas in which additionally or alternatively to the first coating 5 the second coating 7 is provided, the radiation is filtered on the one hand by the first coating 5 and on the other by the second coating 7 so that the second coating 7 overlaps the first coating 5.

FIG. 7 shows (as reference 7') a first example of the second coating 7, in particular in combination with the first coating 5 and/or overlapped by the first coating 5, that is designed so that UV radiation in a wavelength range from 100 to 400 nm and radiation in the blue light range in a wavelength range from 400 to 480 nm is only transmitted with a transmittance of less than 20%, in the illustrated embodiment with a transmittance of 1.5%+5%±0.5%.

The transmission of the second coating 7 shown as 7' in FIG. 7 may correspond to the overall transmission of the radiation transmitted by the radiation device 1, whereby the filter disk 4 used in the radiation device 1 may comprise a full first coating 5 and a partial and/or zonally second coating 7.

The transmission behavior of an alternative second coating 7 is shown as reference 7" in FIG. 7 as well, whereby this second coating 7 also transmits UV radiation in a wavelength range from 320 to 400 nm with a transmittance of greater than 40%. In the illustrated embodiment, the transmittance provided is 55%±5%. Furthermore, both second coatings 7 shown in FIG. 7 transmit radiation with a wavelength of greater than 700 nm with a transmittance of 75%±5%.

Furthermore, the second coating 7 may be designed so that radiation in the red light range in a wavelength range from 600 to 700 nm is transmitted at a transmittance of greater than or equal to 50%. In the embodiment shown in FIG. 7, transmittance for radiation in the red light range of 75%±5% is provided.

In another embodiment of the second coating 7, shown in FIG. 7, a visible color shade other than "red" can be provided instead of radiation in the red light range. According to the embodiment shown in FIG. 7, radiation in the yellow light range at a wavelength range from 560 to 590 nm is transmitted with a transmittance of 75±5% via the second coating 7, if applicable overlapped by the first coating 5.

FIGS. 3 and 4 show that at least one reflector device 10 comprising a reflector 9 is provided. According to the embodiment shown in FIG. 4, a cooling device 11 is provided which is assigned to the reflector device 10. The cooling device 11 comprises in the illustrated embodiment two air spaces between the filter disks 4. The source of radiation 2 is arranged in the area of the reflector 9.

Figure 9:
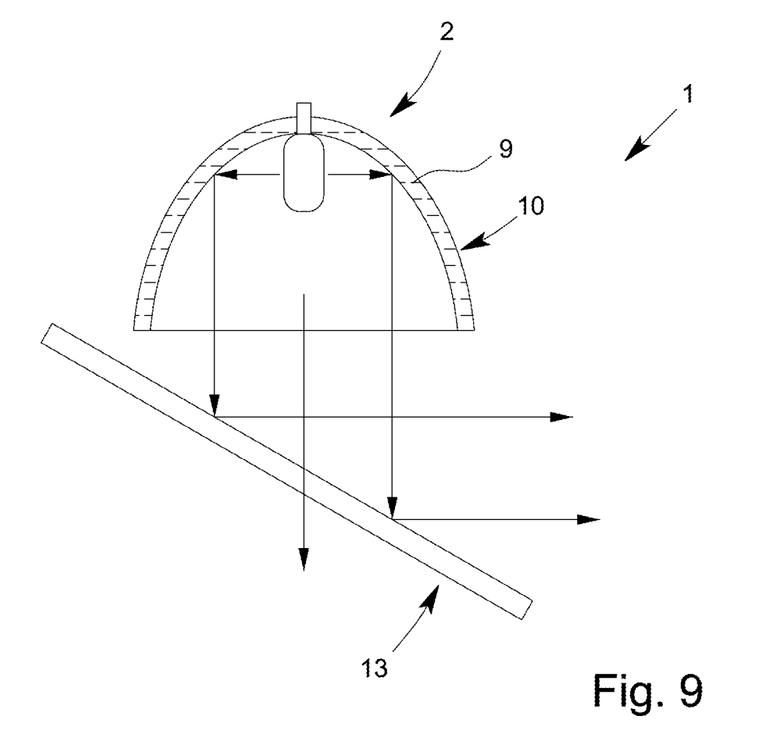
FIG. 9 shows a schematic illustration of a further embodiment of a radiation device according to the invention

Alternatively or additionally to a first coating 5 and a second coating 7, the filtering device 3 may comprise a slanted filter mirror 13, as shown in FIG. 9. The filter mirror 13 shown in FIG. 9 is designed so that radiation in the wavelength range from 280 to 400 nm, i.e., radiation in the UV range, preferably from 280 to 320 nm, is reflected and in particular emitted. Furthermore, the filter mirror 13 is designed so that radiation in the red light wavelength range from 600 to 700 nm can be reflected and/or emitted. Furthermore, radiation in the wavelength range above 700 nm can be reflected, in particular emitted. Further radiation may otherwise be transmitted and/or absorbed, in particular filtered, by the filter mirror 13. The reflection factor here may be greater than or equal to 40%, preferably between 50 and 70%.

Figure 8:
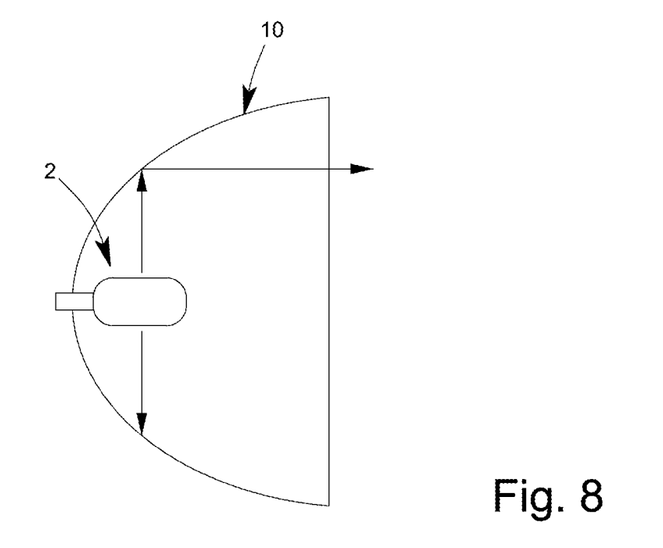
FIG. 8 shows a schematic view of a reflector device according to the invention.

FIG. 8 shows as well that the reflector unit 10 reflects, and in particular emits, radiation in the wavelength range from 100 to 480 nm, preferably in a wavelength range from 280 to 400 nm, and/or in a wavelength range from 600 to 700 nm and/or in the wavelength range of greater than 700 nm. The reflection factor here may be greater than or equal to 40%, preferably between 50 and 70%. Otherwise, the reflector device 10 may transmit and/or absorb, in particular block, the radiation. Consequently, the reflector device 10 and/or the reflector 9 may be designed so that only radiation in the UV-A and/or UV-B range and/or radiation in the red light range and/or infrared radiation with a wavelength of greater than 700 nm is emitted and/or reflected by the reflector device 10.

What is not shown is that the reflector 9 comprises the first and/or second coating 5, 7 so that only the desired wavelength ranges of the radiation are reflected. What is not shown either is that the reflector device 10 may comprise a reflection means that is designed so that the radiation emitted by the source of radiation 2 at least essentially hits the reflector 9 entirely.

What is not shown is that the filtering device 3, preferably the filter disk 4, comprises at least one fluorescing layer. The fluorescing layer can, under radiation, preferably UV radiation in a wavelength range from 280 to 400 nm, emit radiation in the red light range in a wavelength range from 600 to 700 nm. The fluorescing layer may, in particular, be designed as a partial layer. The fluorescing layer may be arranged on the back side 8 of the filter disk 4, facing away from the source of radiation 2. The fluorescing layer may, in particular, be firmly bonded to the first coating 5.

The source of radiation 2 provided may be a radiation lamp, in particular a high-pressure and/or maximum-pressure gas discharge lamp.

FIGS. 1 and 2 show a ballast 14 which may be controllable or not controllable. The source of radiation 2 may be capable of being dimmed by means of the ballast 14. In particular, a magnetic or electronic ballast 14 may be provided.

The invention claimed is:

1. A radiation device for the radiation of human skin, including at least with radiation in the red light range, with a source of radiation and a filtering device for filtering the radiation emitted by the source of radiation;
    wherein the filtering device comprises a filter disk, and wherein the filter disk comprises a first coating, wherein the first coating is arranged on a front side of the filter disk facing the source of radiation, wherein the first coating is provided as a layer across the entire surface of the filter disk, and wherein the first coating is designed so that radiation is transmitted in at least one of the wavelength range from 280 to 400 nm, a wavelength range from 600 to 700 nm, and a wavelength of greater than 700 nm;
    wherein the filter disk comprises a second coating arranged on the first coating, wherein the second coating is formed as a partially formed layer, wherein the second coating is designed to filter the radiation in at least one wavelength range of a visible color shade of the visible light spectrum and to emit only zonally radiation in a wavelength range of a visible color shade of the visible light spectrum to indicate operation of the radiation device; and
    wherein the filtering device is configured in such a way that the radiation device emits radiation in a wavelength range from 280 to 400 nm and beyond that radiation in a wavelength range of 600 to 700 nm.

2. The radiation device according to claim 1, wherein the filtering device is able to filter radiation with a wavelength below 280 nm.

3. The radiation device according to claim 1, wherein the first coating is designed so that radiation is transmitted with a transmission greater than or equal to 50% for radiation in the at least one of the wavelength range from 280 to 400 nm, the wavelength range from 600 to 700 nm, and the wavelength of greater than 700 nm.

4. The radiation device according to claim 1, wherein the filter disk absorbs radiation in the UV-C range, and wherein the degree of absorption is greater than 0.5.

5. The radiation device according to claim 1, wherein the first coating is designed so that UV-B radiation in a wavelength range from 280 to 320 nm is transmitted with a transmittance of less than or equal to 50%.

6. The radiation device according to claim 1, wherein the first coating is designed so that radiation in a wavelength range from 320 to 400 nm is transmitted with a transmittance of greater than or equal to 40%.

7. The radiation device according to claim 1, wherein the first coating is designed so that radiation in the blue light range in a wavelength range from 400 to 480 nm is transmitted with a transmittance of greater than or equal to 20%.

8. The radiation device according to claim 1, wherein the second coating is firmly bonded to the first coating.

9. The radiation device according to claim 1, wherein the second coating is designed to transmit radiation in at least one of the green light, red light, and yellow light range.

10. The radiation device according to claim 1, wherein the second coating is designed so that radiation in at least one of a wavelength range from 100 to 400 nm and a wavelength range between 400 and 480 nm is transmitted with a transmittance of less than or equal to 20%.

11. The radiation device according to claim 1, wherein the second coating is designed so that radiation in at least one of the wavelength range from 600 to 700 nm and a wavelength range of greater than 700 nm is transmitted with a transmittance of greater than or equal to 50%.

12. The radiation device according to claim 1, wherein the second coating is designed so that radiation in a wavelength range from 320 to 400 nm is transmitted with a transmittance of greater than or equal to 40%.

13. The radiation device according to claim 1, further comprising a reflector device having a reflector, and wherein the source of radiation is arranged in the area of the reflector.

14. The radiation device according to claim 1, wherein the filtering device comprises a slanted filter mirror that reflects radiation in at least one of a wavelength range from 280 to 400 nm, the wavelength from 600 to 700 nm, and a wavelength range above 700 nm, and wherein the filter mirror otherwise at least one of transmits and absorbs.

15. A radiation device according to claim 1, further comprising a reflector device that reflects radiation in at least one of a wavelength range from 100 to 480 nm, the wavelength range from 600 to 700 nm, and a wavelength range of greater than 700 nm, and wherein the reflector device otherwise at least one of transmits and absorbs.

16. The radiation device according to claim 1, wherein the filter device comprises at least one fluorescing layer, wherein the fluorescing layer emits under radiation in the wavelength range from 600 to 700 nm.

17. The radiation device according to claim 16, wherein the fluorescing layer is designed as a partial layer, and wherein the fluorescing layer is arranged on a back side of the filter disk facing away from the source of radiation.

18. The radiation device according to claim 1, wherein the second coating is farther than the first coating from the radiation source.

19. The radiation device according to claim 18, wherein radiation with a wavelength of greater 700 nm is transmitted, and wherein the second coating otherwise at least one of reflects and absorbs.

20. The radiation device according to claim 16, wherein the fluorescing layer is designed as a partial layer, and wherein the fluorescing layer is bonded to the first coating.

* * * * *